United States Patent
Yarnykh

(10) Patent No.: US 10,617,343 B2
(45) Date of Patent: Apr. 14, 2020

(54) METHODS AND SYSTEMS FOR QUANTITATIVE BRAIN ASSESSMENT

(71) Applicant: University of Washington, Seattle, WA (US)

(72) Inventor: Vasily L. Yarnykh, Edmonds, WA (US)

(73) Assignee: University of Washington, Seattle, WA (US)

( * ) Notice: Subject to any disclaimer, the term of this patent is extended or adjusted under 35 U.S.C. 154(b) by 1198 days.

(21) Appl. No.: 14/931,303

(22) Filed: Nov. 3, 2015

(65) Prior Publication Data

US 2016/0120456 A1 May 5, 2016

Related U.S. Application Data

(60) Provisional application No. 62/074,480, filed on Nov. 3, 2014.

(51) Int. Cl.
*A61B 5/00* (2006.01)
*A61B 5/055* (2006.01)
*A61N 1/40* (2006.01)

(52) U.S. Cl.
CPC ............ *A61B 5/4064* (2013.01); *A61B 5/055* (2013.01); *A61B 5/407* (2013.01); *A61B 5/4869* (2013.01); *A61N 1/40* (2013.01)

(58) Field of Classification Search
CPC ....... A61B 5/055; A61B 5/4064; A61B 5/407; A61B 5/4869; G01R 33/5605; G01R 33/246; G01R 33/4608; G01R 33/4828
See application file for complete search history.

(56) References Cited

U.S. PATENT DOCUMENTS

| | | | |
|---|---|---|---|
| 7,292,039 B1* | 11/2007 | Laub | G01R 33/4828 324/309 |
| 9,547,059 B2* | 1/2017 | Greiser | G01R 33/50 |
| 9,594,145 B2* | 3/2017 | Lee | G01R 33/246 |
| 2004/0046557 A1* | 3/2004 | Karmarkar | G01R 33/287 324/322 |

(Continued)

OTHER PUBLICATIONS

Childs AM, et al. "Cerebral Maturation in Premature Infants: Quantitative Assessment Using MR Imaging," AJNR Am J Neuroradiol, 2001;22:1577-82.

(Continued)

*Primary Examiner* — Baisakhi Roy
(74) *Attorney, Agent, or Firm* — McDonnell Boehnen Hulbert & Berghoff LLP

(57) ABSTRACT

Systems and methods for measuring macromolecular proton fraction in a subject are provided. A nuclear magnetic resonance apparatus applies a magnetic field to a body region on the subject, and radiofrequency modes are applied to the body region as well. Each radiofrequency mode delivers a plurality of radiofrequency pulses separated by time delays, wherein at least one of the radiofrequency modes causes suppression of signal components from an unwanted tissue, and at least one of the radiofrequency modes causes magnetization exchange between water and macromolecules in tissues in the body region. Amplitudes corresponding to magnetic signals received from the body region are measured and macromolecular proton fraction based on the amplitudes can be calculated.

21 Claims, 14 Drawing Sheets

(56) References Cited

U.S. PATENT DOCUMENTS

| | | | |
|---|---|---|---|
| 2006/0064138 A1* | 3/2006 | Velasco | A61N 1/36096 607/42 |
| 2006/0080044 A1* | 4/2006 | Ropele | G01R 33/563 702/23 |
| 2010/0142784 A1* | 6/2010 | Yarnykh | G01R 33/4608 382/131 |
| 2012/0197105 A1* | 8/2012 | Mezer | A61B 5/055 600/410 |
| 2013/0082708 A1* | 4/2013 | Yokosawa | A61B 5/055 324/309 |
| 2015/0223703 A1* | 8/2015 | Abd-Elmoniem | A61B 5/7207 600/413 |
| 2016/0018496 A1* | 1/2016 | Van Zijl | A61B 5/055 324/309 |

OTHER PUBLICATIONS

Deoni SC, et al. "High-Resolution T1 and T2 Mapping of the Brain in a Clinically Acceptable Time with DESPOT1 and DESPOT2," MRM 2005;53:237.

Dula AN, et al. "Multi-exponential T2, Magnetization Transfer and Quantitative Histology in White Matter Tracts of Rat Spinal Cord," MRM 2010;63:902.

Huppi PS, et al. "Quantitative Magnetic Resonance Imaging of Brain Development in Premature and Mature Newborns," Ann Neurol 1998; 43:224-35.

Miller AK, et al. "Variation with age in the volumes of grey and white matter in the cerebral hemispheres of man: measurements with an image analyser," Neuropathol Appl Neurobiol 1980; 6:119-32.

O'Brien JS, Sampson EL. "Lipid composition of the normal human brain: gray matter, white matter and myelin," J Lipid Res 1965; 6:537-44.

Ou X, et al. "The MT pool size ratio and the DTI radial diffusivity may reflect the myelination in shiverer and control mice," NMR Biomed 2009;22:480.

Petrie EC, et al. "Neuroimaging, Behavioral, and Psychological Sequelae of Repetitive Combined Blast/Impact Mild Traumatic Brain Injury in Iraq and Afghanistan War Veterans," J Neurotrauma 2014; 31:425-36.

Pruessmann KP, et al. "SENSE: Sensitivity Encoding for Fast MRI," MRM 1999;42:952.

Samsonov A, et al. "Quantitative MR Imaging of Two-Pool Magnetization Transfer Model Parameters in Myelin Mutant Shaking Pup," Neuroimage 2012; 62:1390-8.

Skinner TE, Glover GH. "An Extended Two-Point Dixon Algorithm for Calculating Separate Water, Fat, and B[sub 0], Images," MRM 1997;37:628.

Thiessen JD, et al. "Quantitative MRI and ultrastructural examination of the cuprizone mouse model of demyelination," NMR Biomed 2013; 26:1562-81.

Underhill HR, et al. "Fast Bound Pool Fraction Imaging of the In Vivo Rat Brain: Association with Myelin Content and Validation in the C6 Glioma Model," Neuroimage 2011; 54:2052-65.

Yarnykh VL, et al. "Fast Macromolecular Proton Fraction Mapping from a Single Off-resonance Magnetization Transfer Measurement," Magn Reson Med 2012; 68:166-78.

Yarnykh VL. "Actual Flip-Angle Imaging in the Pulsed Steady State: A Method for Rapid Three-Dimensional Mapping of the Transmitted Radiofrequency Field," MRM 2007;57:192.

* cited by examiner

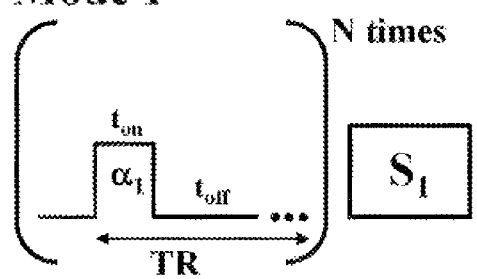
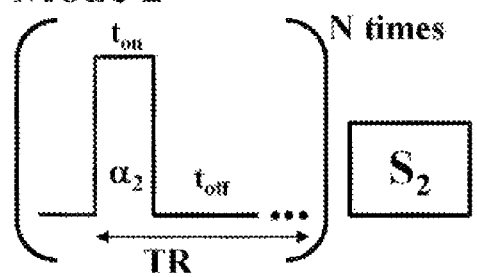
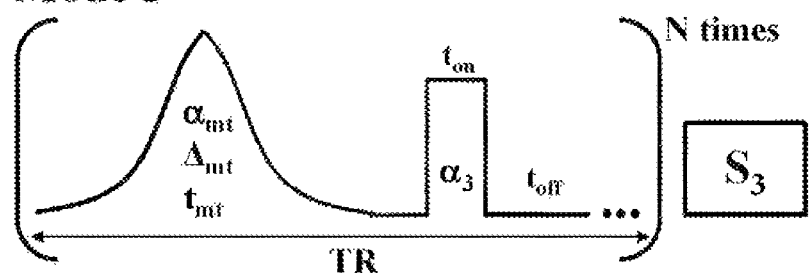
Figure 3

Table 1
Comparison Between MPF Measurements with Acquired and
Synthetic Reference Images in Segmented Brain Tissues

| Value | WM | GM |
|---|---|---|
| Mean MPF with acquired reference (%) | 12.77 ± 0.41 | 6.73 ± 0.15 |
| Mean MPF with synthetic reference (%) | 12.86 ± 0.31 | 6.68 ± 0.14 |
| Mean difference (bias) (%) | −0.09 ± 0.16 | 0.05 ± 0.18 |
| Limits of agreement (%) | −0.41; 0.23 | −0.30; 0.41 |
| Significance for the bias ($P$) | 0.16 | 0.44 |
| Significance for inequality of variances ($P$) | 0.61 | 0.64 |
| Within-subject coefficient of variation (%) | 0.99 | 1.86 |

Figure 10

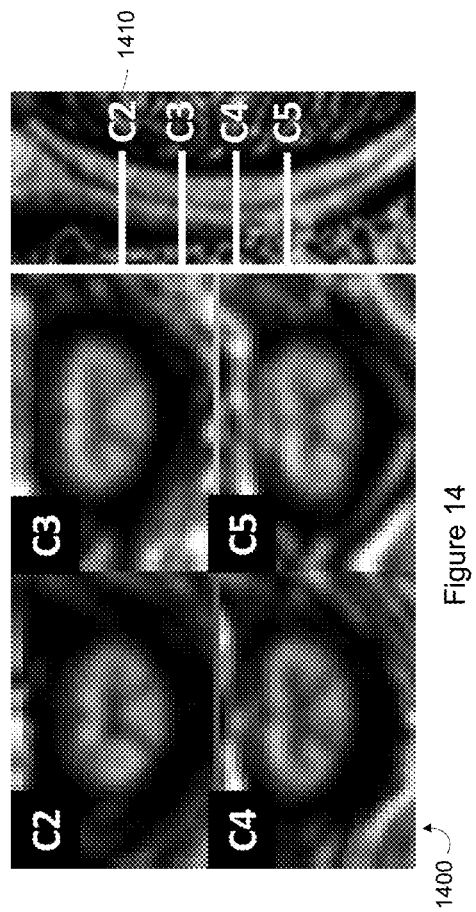

METHODS AND SYSTEMS FOR QUANTITATIVE BRAIN ASSESSMENT

CROSS-REFERENCE TO RELATED APPLICATIONS

This application claims priority to U.S. Provisional Patent Application Ser. No. 62/074,480 filed on Nov. 3, 2014, which is hereby incorporated by reference in its entirety.

STATEMENT REGARDING FEDERALLY SPONSORED RESEARCH

This invention was made with U.S. government support under Grant No. R21EB016135, awarded by the National Institutes of Health. The U.S. government has certain rights in the invention.

BACKGROUND

Myelination, which is the production of the myelin sheath, can be viewed as a morphological criterion of the functional maturity of neural conduction in the brain. Cerebral myelination begins before birth, and is not completed until late in adolescence.

The assessment of cerebral myelination is useful for a number of functions. Cerebral myelination at various life stages may be observed and monitored. Additionally, a number of neurological diseases, where the loss of myelin slows or blocks nerve conduction, may be diagnosed, monitored, and be subject to prognostic assessment through observing and measuring brain and spinal cord myelination. Such diseases include multiple sclerosis (MS), brain trauma, stroke, and many other conditions.

Magnetic resonance imaging (MRI) is a widely used medical imaging modality that provides soft-tissue differentiation to assess cerebral myelination in a subject in vivo. However, clinical MRI scanners, especially the superconducting magnet and magnetic field gradient hardware of MRI scanners, are too costly to use in population studies or in low-resource healthcare facilities.

SUMMARY

In accordance with the present invention, a system and a method are defined for measuring macromolecular proton fraction in a subject. In one embodiment, the method may comprise applying, via a nuclear magnetic resonance apparatus, a magnetic field to a body region on the subject and applying a plurality of radiofrequency (RF) modes to the body region. Each RF mode comprises delivering a plurality of RF pulses separated by at least one time delay such that (i) at least one of the plurality of RF modes causes suppression of signal components from an unwanted tissue in the body region, and (ii) at least one of the plurality of RF modes causes magnetization exchange between water and macromolecules in tissues in the body region. Amplitudes are then measured corresponding to a plurality of magnetic signals received from the body region, and macromolecular proton fraction in the body region is calculated based on the measured amplitudes. In some embodiments, the body region may encompass the brain or the spinal cord in the subject. An unwanted tissue may be a tissue that does not belong to the brain. The unwanted tissue may be a fat tissue, a muscle tissue, or a cerebrospinal fluid. The subject may be an adult, an adolescent, an infant, or a newborn infant.

Delivering the plurality of RF pulses separated by at least one time delay may cause one or more of the following: (i) a saturation of a nuclear magnetization of fat protons outside the brain; (ii) a saturation of a nuclear magnetization of muscle protons outside the brain; (iii) a saturation of a nuclear magnetization of cerebrospinal fluid protons inside the brain; (iv) a variable excitation of a nuclear magnetization of protons of the brain; and (v) a variable saturation of a nuclear magnetization of macromolecular protons in the brain parenchyma.

In some embodiments, measuring amplitudes corresponding to the plurality of magnetic signals is performed after varying one or more of the following: (i) the excitation of a nuclear magnetization of protons of the brain; (ii) the saturation of the nuclear magnetization of macromolecular protons in the brain parenchyma; and (iii) a duration of the time delay separating the RF pulses.

In some embodiments, measuring amplitudes corresponding to a plurality of magnetic signals further comprises varying one or more of the following: (i) an excitation of a nuclear magnetization of protons in the body region; (ii) a saturation of a nuclear magnetization of macromolecular protons in the body region; and (iii) a duration of the at least one time delay separating the plurality of RF pulses.

Myelin content in the body region may be determined based on the macromolecular proton fraction.

In another embodiment, a magnetic resonance apparatus is provided and comprises a magnet configured to apply a magnetic field to a body region on a subject, an RF pulse generator configured to deliver RF pulses to the body region, and a controller comprising a processor and a non-transitory computer-readable medium configured to store program instructions thereon executable by the processor to cause the controller to perform functions comprising: applying the magnetic field to the body region, applying a plurality of RF modes to the body region, wherein each RF mode comprises delivering the plurality of RF pulses separated by at least one time delay, such that the said plurality of RF pulses causes suppression of signal components from an unwanted tissue in the body region for at least one of the plurality of RF modes and magnetization exchange between water and macromolecules in tissues in the body region for at least one of the plurality of RF modes, measuring amplitudes corresponding to a plurality of magnetic signals received from the body region, and calculating macromolecular proton fraction values of the body region based on the measured amplitudes.

These as well as other aspects and advantages of the synergy achieved by combining the various aspects of this technology, that while not previously disclosed, will become apparent to those of ordinary skill in the art by reading the following detailed description, with reference where appropriate to the accompanying drawings.

BRIEF DESCRIPTION OF THE FIGURES

FIG. 3 depicts a diagram of RF amplitudes corresponding to a plurality of RF pulses in accordance with at least one embodiment;

FIG. 10 depicts a table illustrating a comparison between MPF measurements with acquired and synthetic reference images in segmented brain tissues in accordance with at least one exemplary embodiment;

FIG. 14 depicts images of anatomic appearance of WM and GM on MPF maps of the cervical spinal cord at different levels in accordance with at least one exemplary embodiment;

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Macromolecular proton fraction (MPF) is a biophysical parameter determining the efficiency of magnetization transfer (MT) between water and macromolecules in tissues. MPF is a sensitive and accurate non-invasive measure of myelin in neural tissues and is based on the strong linear correlation between MPF and histologically determined myelin density. Thus, MPF may be considered to be used as a myelin biomarker in clinical applications. The present disclosure provides a time-efficient, high-resolution method for in vivo MPF measurements in the human brain and spinal cord.

While cerebral myelination can be assessed using modern MRI methods, clinical MRI scanners are too costly to use in population studies or in locations with low financial resources, such as rural healthcare facilities and developing countries. The present disclosure is based on a whole-brain measurement of the specific biophysical parameter, MPF, from a non-localized magnetic resonance signal. By obtaining a whole-brain measurement from a non-localized magnetic resonance signal, the more expensive components present in clinical MRI scanners can be eliminated. Thus, the methods and systems described herein allow for the establishment of a trajectory of brain development across a wide age range and can be reliably implemented in low-resource settings.

Figure 1:
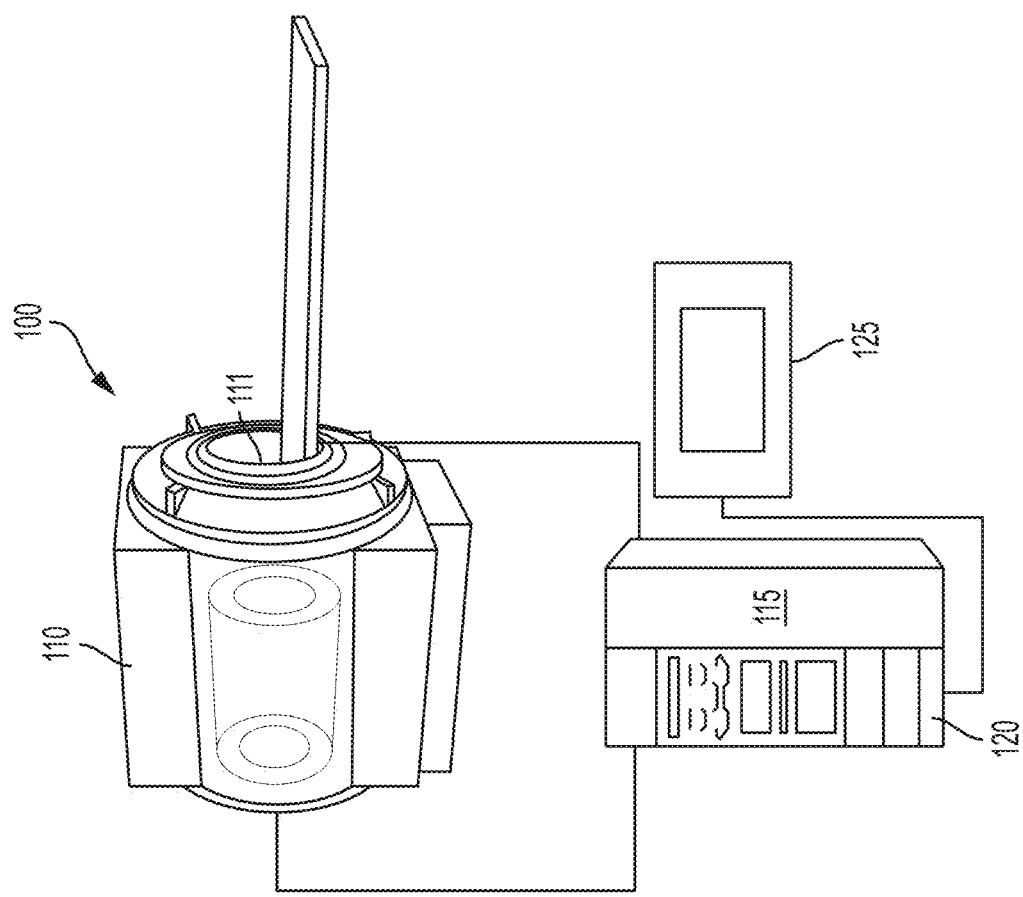
FIG. 1 depicts a schematic of an exemplary system in accordance with at least one embodiment.

FIG. 1 depicts a schematic of an exemplary system 100 in accordance with at least one embodiment. The system 100 may be used, among other things, to measure MPF in a subject. Thus, the system 100 may be used on a subject in vivo. As referenced herein, a subject may be a human subject, and may be an adult human subject, an adolescent human subject, an infant human subject, or a newborn human subject.

In FIG. 1, an MRI system is shown as system 100. The system 100 may include a magnet 110, an RF pulse generator 115, a controller 120, and a display 125. A sample to be imaged may be placed through the access 111 to be properly positioned for exposure to the magnet 110.

The system 100 provides for a non-localized, non-invasive measurement of the myelin content of a body region. The system 100 may implement low-cost hardware, avoiding the more expensive components that are generally present in clinical MRI equipment (e.g., a superconducting magnet and magnetic field gradient hardware). Advantageously, even with low-cost hardware, the system 100 can be used to quickly obtain a high-resolution macromolecular proton fraction of a sample. With the exception of the magnet 110, the electronic components of the system 100 enable a compact tabletop design. The system 100 includes low power consumption and may have a total weight less than 100 kg, enabling installation in any low-resource setting or manufacturing the system as a mobile unit on a vehicle platform.

In FIG. 1, the magnet is shown within a standard MRI structure providing the access 111 through which a sample can be placed for exposure to a magnetic field and subsequent analysis.

In one example embodiment, the magnet 110 is configured to produce a static and substantially uniform magnetic field encompassing the sample, which may include a body region of a subject. While in some embodiments the magnet 110 may be a superconducting magnet, the system 100 does not need implementation of a magnetic field gradient for spatial localization of a signal; thus, a low-cost, low-field magnet can achieve the desired results as the magnet 110. For example, the magnet 110 may be a low-field Halbach array magnet having a 0.1-0.2 Tesla magnetic field induction and producing a homogeneous magnetic field volume of, for example, a standard adult head size. In certain embodiments, the magnet 110 may also contain an appropriate transmit-receive RF coil and a dedicated pulse programming module, facilitating implementation of the method 200 of FIG. 2 below.

The RF pulse generator 115 is configured to deliver RF pulses to a body region of a subject.

The controller 120 may be a programmable radiofrequency controller (PRC) comprising a processor coupled to a receiver, data storage, and logic. These elements may be coupled by a system or bus or other mechanism. The processor may include one or more general-purpose processors and/or dedicated processors, and may be configured to perform an analysis on received and/or stored data. The controller 120 may be further configured to measure amplitudes corresponding to a plurality of magnetic signals received from the body region and to calculate macromolecular proton fraction in the body region based on the measured amplitudes.

An output interface of the controller 120 may be configured to transmit output from the controller 120 to the display 125. The display 125 may be any interface configured to display an output, such as data, maps, graphs, and images, for example.

In one embodiment, the system 100 may measure an MPF in the brain of a subject and compare the MPF with a control. In one example embodiment, a control includes a range of values of the MPF that is normal for a certain age of the subject. Such a comparison may be used to diagnose a demyelinating disease, for example.

In another embodiment, the system 100 may measure an MPF in a body region of a subject and determine a myelin content for the body region.

Figure 2:
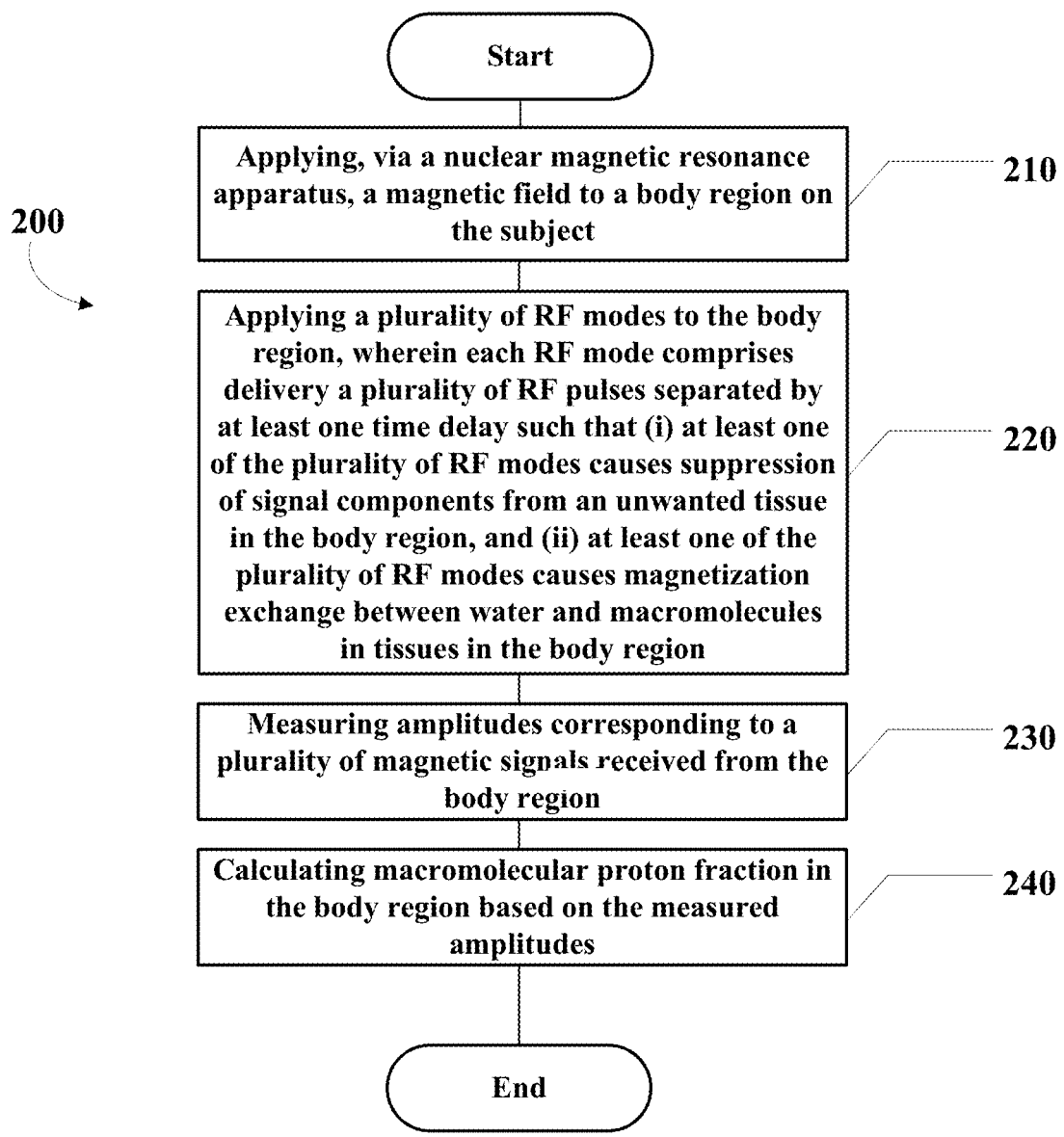
FIG. 2 depicts a simplified flow diagram of an example method that may be carried out to measure MPF in a subject in accordance with at least one embodiment.

FIG. 2 depicts a simplified flow diagram of an example method 200 that may be carried out to measure MPF in a subject, in accordance with at least one embodiment. Method 200 presents an embodiment of a method that, for example, could be used with the system 100.

In addition, for the method 200 and other processes and methods disclosed herein, the flowchart shows functionality and operation of one possible implementation of the present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include a physical and/or non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, or other article of manufacture, for example. Alternatively, program code, instructions, and/or data structures may be transmitted via a communications network via a propagated signal on a propagation medium (e.g., electromagnetic wave(s), sound wave(s), etc.).

The method 200 allows for determining MPF in a body region of a subject. The method 200 may be used to quantitatively characterize brain myelination and to observe brain development across a wide age range, from early infancy to adulthood. The method 200 may additionally be used in infancy or childhood to predict capacities thought to contribute to adult productivity and intelligence.

Initially, the method 200 includes applying, via a nuclear magnetic resonance apparatus, a magnetic field to a body region on a subject, at block 210. The magnetic field may be delivered from a nuclear magnetic resonance apparatus comprising a magnet, such as the MRI device with the magnet 110 of FIG. 1, in one example embodiment. In operation, a subject is positioned at a designated location within the MRI device (e.g., through the access 111 of FIG. 1) to allow for a body region to be exposed to the magnet 110. The magnet 110 then emits a magnetic field, which is applied to the body region of the subject. The body region may comprise the brain and/or the spinal cord in some embodiments, and is observed in vivo.

The method 200 then includes applying a plurality of RF modes to the body region, at block 220. Each RF mode comprises delivering a plurality of RF pulses separated by at least one time delay such that (i) at least one of the plurality of RF modes causes suppression of signal components from an unwanted tissue in the body region, and (ii) at least one of the plurality of RF modes causes magnetization exchange between water and macromolecules in tissues in the body region.

The plurality of RF pulses may comprise a sequence, and may be pre-programmed into a computing system, such as the controller 120 of FIG. 1. The plurality of RF pulses suppresses signals from unwanted tissues, for example non-brain tissues, without the use of magnetic field gradients, while allowing detection of the MT effect on the brain water signal. Specifically, the dual-inversion preparation module with optimized inversion times is applied to suppress signal contributions from non-brain tissues such as cerebrospinal fluid (CSF) and subcutaneous fat. Contributions from the muscle tissue and scalp skin can also be suppressed using spin-echo signal readout with a sufficiently long echo time, because these tissues have much shorter relaxation times ($T_2$) than brain white and gray matter. To sensitize this sequence to the MT effect, a series of off-resonance saturation pulses can be applied through sequence delays. A reference measurement for signal normalization may be performed using the same sequence without saturation pulses. A saturation-recovery sequence with the same preparative modules may be used to measure global brain longitudinal relaxation time ($T_1$).

The method 200 then includes measuring amplitudes corresponding to a plurality of magnetic signals received from the body region, at block 230.

The method 200 includes calculating MPF in the body region based on the measured amplitudes, at block 240. Whole-brain MPF is calculated using the model of the pulsed MT effect, with modifications taking into account the effect of prepared RF pulses. Each signal measurement takes about 10-20 seconds (with phase cycling) due to a high signal-to-noise ratio that can be achieved for the whole-brain water signal without magnetic field gradients, resulting in the total signal measurement time comprising about three minutes.

In one exemplary embodiment, the method 200 operates by applying three RF modes generated in any order by a programmable RF controller of a magnetic resonance apparatus. A schematic diagram 300 of a plurality of RF amplitudes corresponding to a plurality of RF pulses generated in each mode is depicted in FIG. 3. In the first mode, identical on-resonance RF pulses with a flip angle $\alpha_1$ and duration $t_{on}$ separated by a delay $t_{off}$ are applied to the body region until the magnetization reaches the steady state, and a steady-state magnetic resonance signal $S_1$ is recorded. In the second mode, a similar sequence of RF pulses with a flip angle $\alpha_2$ is applied, and a signal $S_2$ is recorded. In the third mode, two RF pulses are applied in rapid succession: a first pulse is an off-resonance magnetization transfer saturation pulse with an offset frequency $\Delta_{mt}$, flip angle $\alpha_{mt}$, and duration $t_{mt}$; and a second pulse is an on-resonance pulse with a flip angle $\alpha_3$ and duration $t_{on}$. The pulse blocks are separated by a delay $t_{off}$ that is adjusted to limit the specific absorption rate in an object and may or may not be equal to the delay $t_{off}$ applied in the first and the second modes. Similar to the first and the second mode, the sequence in the third mode is repeated until the magnetization reaches the steady state, and a signal $S_3$ is recorded after an on-resonance pulse.

To compute MPF from recorded signals $S_1$, $S_2$, and $S_3$, the following algorithm is used. The steady-state signals recorded in the first and second modes of operation obey the Ernst equation:

$$S_{1,2} = PD \frac{1-\exp(-TR/T_1)}{1-\cos\alpha_{1,2}\exp(-TR/T_1)} \sin\alpha_{1,2}, \qquad [1]$$

where PD is the proton density, TR is the repetition time, $TR = t_{on} + t_{off}$, and $T_1$ is the longitudinal relaxation time. Accordingly, parameters $T_1$ and PD are calculated from signals $S_1$ and $S_2$. The signal $S_3$ is dependent on magnetization transfer between free water protons and macromolecular protons caused by an off-resonance saturation pulse and can be expressed as:

$$S_3 = PD M_z^F \sin\alpha_3, \qquad [2]$$

where $M_z^F$ is the normalized steady-state longitudinal magnetization of free water protons $M_z^F$ that is related to MPF and pulse sequence parameters through the matrix equation of pulsed magnetization transfer:

$$M_z = (I - E_s E_m E_r C)^{-1}\{[E_s E_m (I-E_r) + (I-E_s)]M_{eq} + E_s(I-E_m)M_{ss}\}, \qquad [3]$$

where $M_z$ is the vector with components $M_z^F$ and $M_z^B$ corresponding to the longitudinal magnetization of the free and bound (macromolecular) proton pools immediately before the excitation pulse; $M_{eq}$ is the vector of equilibrium magnetization with elements 1-f and f, where f is MPF; $M_{ss}$ is the vector of steady-state longitudinal magnetization for which the explicit notation can be found, for example, in Yarnykh, V. L. et al., *Cross-Relaxation Imaging Reveals Detailed Anatomy of White Matter Fiber Tracts in the Human Brain*, Neuroimage 2004; 23: 409-424; I is the unit matrix; the matrix term $E_m = \exp((R_L + W)t_{mt})$ describes off-resonance saturation by the pulse with duration $t_{mt}$; the terms $E_s = \exp(R_L t_s)$ and $E_r = \exp(R_L t_{off})$ describe longitudinal relaxation during delays before ($t_s$) and after ($t_{off}$) the excitation pulse; and the diagonal matrix $C = \text{diag}(\cos\alpha_3, 1)$ corresponds to instant rotation of the magnetization $M_z^F$ by the excitation pulse with the flip angle $\alpha_3$. The longitudinal relaxation matrix $R_L$ and saturation matrix W are defined as follows:

$$R_L = \begin{bmatrix} -R_1^F - k & k(1-f)/f \\ k & -R_1^B - k(1-f)/f \end{bmatrix}, \qquad [4]$$

$$W = -\text{diag}(W^F, W^B),$$

where $R_1^{F,B} = 1/T_1$ are the longitudinal relaxation rates of the free and bound pool, which are assumed to be equal; k is the cross-relaxation rate constant defined for MT from free to bound pool; and $W^{F,B}$ are the time-averaged saturation rates:

$$W^{F,B} = \pi\omega_{1rms}^2 g^{F,B}(\Delta, T_2^{F,B}), \qquad [5]$$

which are calculated via the absorption lineshapes of the pools $g^{F,B}(\Delta, T_2^{F,B})$ and the root-mean-square amplitude of the saturation pulse $\omega_{1rms}$ averaged over the pulse duration. The functions $g^{F,B}(\Delta, T_2^{F,B})$ are determined by the offset frequency $\Delta$ and intrinsic $T_2$ of each pool. The lineshapes $g^{F,B}(\Delta, T_2^{F,B})$ of the free and bound pool are defined by the Lorentzian and superLorentzian functions, respectively. The saturation power $\omega_{1rms}$ is related to the flip angle of the saturation pulse, $\alpha_{MT}$:

$$\omega_{1\,rms} = \frac{\alpha_{MT}}{t_m} \frac{\pi}{180} \frac{\left(\int_0^{t_m} b_1^2(t)dt\right)^{1/2}}{\int_0^{t_m} b_1(t)dt}, \qquad [6]$$

where $b_1(t)$ is the pulse envelope function normalized to the area of the rectangular pulse with the same duration and peak amplitude. As described in Yarnykh V. L., *Fast Macromolecular Proton Fraction Mapping From a Single Off-Resonance Magnetization Transfer Measurement*, Magnetic Resonance Medicine 2012; 68(1): 166-178, equation [3] can be iteratively solved relative to MPF with appropriate constraints applied to other model parameters. In the described exemplary embodiment, the signal $S_3$ is normalized to the parameter PD and is used as an input variable together with $T_1$ to compute MPF in a body region. In the described exemplary embodiment, a signal from a fatty tissue can be effectively removed by either applying water-selective excitation pulses or repeating each radiofrequency mode twice with a delay $t_{off}$ chosen such that water and fat signals appear either in the same or in opposite phase. In the last modification, complex summation of two signals results in cancellation of an unwanted signal from fat.

Figure 4:
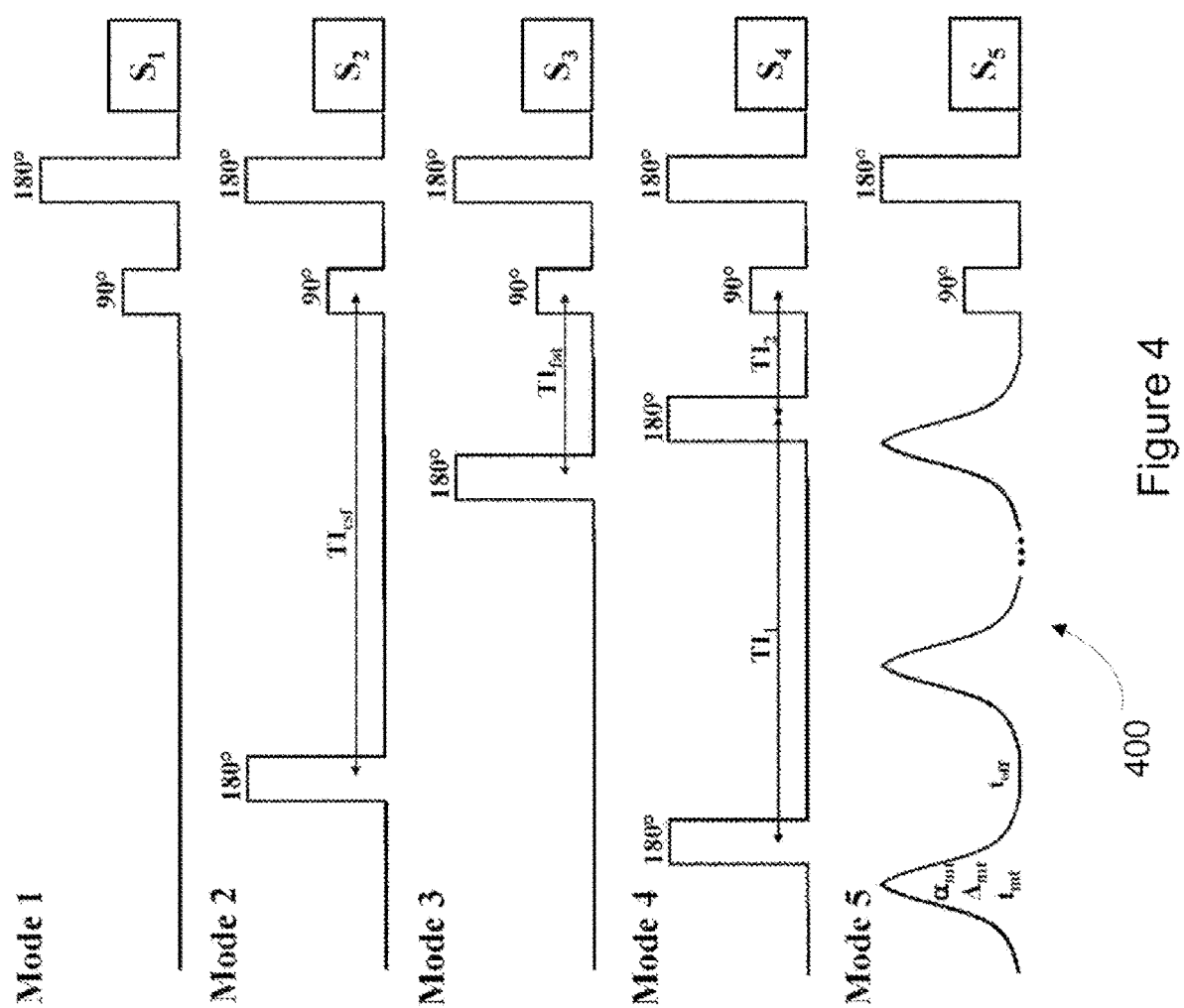
FIG. 4 depicts a diagram of RF amplitudes corresponding to a plurality of RF pulses in accordance with at least one embodiment.

In another exemplary embodiment, the method 200 operates by applying five radiofrequency modes generated in any order by a programmable radiofrequency controller of a magnetic resonance apparatus. A schematic diagram 400 of radiofrequency amplitudes corresponding to a plurality of radiofrequency pulses generated in each mode is depicted in FIG. 4. In the first mode, a fully relaxed spin-echo signal $S_1$ is recorded from an object by applying a radiofrequency pulse with 90° flip angle followed by a radiofrequency pulse with 180° flip angle. In the second mode, a 180° inversion pulse is executed prior to the spin-echo module with an inversion delay $TI_{csf}$ chosen to null a signal from cerebrospinal fluid, and a spin-echo signal $S_2$ is recorded. In the third mode, a 180° inversion pulse is executed prior to the spin-echo module with an inversion delay $TI_{fat}$ chosen to null a signal from fatty tissue, and a spin-echo signal $S_3$ is recorded. In the fourth mode, two 180° inversion pulses are executed prior to the spin-echo module with two inversion delays $TI_1$ and $TI_2$ chosen to simultaneously null signals from cerebrospinal fluid and fatty tissue, and a spin-echo signal $S_4$ is recorded. In the fifth mode, a continuous train of off-resonance magnetization transfer saturation pulses with an offset frequency $\Delta_{mt}$, flip angle $\alpha_{mt}$, duration $t_{mt}$, and inter-pulse delay $t_{off}$ is applied prior to the spin-echo module, and signal $S_5$ is recorded.

If the signals $S_1$, $S_2$, $S_3$, $S_4$, and $S_5$ are acquired from an object containing different tissues, such as a human head, by using appropriate algebraic combinations of these signals, contributions of unwanted tissues, such as fatty tissue, cerebrospinal fluid, and muscle tissue can be effectively removed, and MPF in a brain tissue can be accurately measured. More specifically, in this exemplary embodiment, a signal from muscle tissue can be reduced to a negligible level by using a sufficiently long echo time (TE) for recording a spin-echo signal, because transverse relaxation time $T_2$ of muscle tissue is substantially (at least two-fold) shorter than $T_2$ of brain white and gray matter. To exemplify the elimination of unwanted signal components from fat and cerebrospinal fluid, let us consider mathematical description of signals generated in radiofrequency modes 1 through 5. For the first mode, the signal can be expressed as $$S_1 = PD_b + PD_{fat} + PD_{csf} \quad [7]$$

where $PD_b$ is the proton density of brain tissue, $PD_{fat}$ is the proton density of fatty tissue, and $PD_{csf}$ is the proton density of cerebrospinal fluid. Note that all proton densities absorb attenuation factors associated with transverse relaxation during TE, which are not explicitly written herein for brevity and do not affect further analysis. For the second mode, the signal does not contain a contribution from cerebrospinal fluid and can be written as:

$$S_2 = PD_b E_1 + PD_{fat} E_{fat} \quad [8]$$

where $E_1$ and $E_{fat}$ are the attenuation factors for brain and fat magnetization associated with the application of an inversion pulse with inversion delay $TI_{csf}$:

$$E_1 = 1 - 2\exp(-TI_{csf}/T_{1b}), \quad [9]$$

$$E_{fat} = 1 - 2\exp(-TI_{csf}/T_{1fat}), \quad [10]$$

where $T_{1b}$ and $T_{1fat}$ are the longitudinal relaxation times of brain and fatty tissues, respectively. Note that $T_1$ of brain is approximated here by a single value, which is in fact a weighted average of $T_1$ values of white and gray matter. For the third mode, where a signal from fat is suppressed, similar consideration gives:

$$S_3 = PD_b E_2 + PD_{csf} E_{csf} \quad [11]$$

where $E_2$ and $E_{csf}$ are the attenuation factors for brain and cerebrospinal fluid magnetization associated with the application of an inversion pulse with inversion delay $TI_{fat}$:

$$E_2 = 1 - 2\exp(-TI_{fat}/T_{1b}) \quad [12]$$

$$E_{csf} = 1 - 2\exp(-TI_{fat}/T_{1csf}) \quad [13]$$

where $T_{1csf}$ is longitudinal relaxation time of cerebrospinal fluid. For the fourth mode, both fat and cerebrospinal fluid signals are eliminated, and a measured signal entirely originates from the brain:

$$S_4 = PD_b E_3, \quad [14]$$

where $E_3$ is the attenuation factor for brain tissue associated with the application of double inversion-recovery:

$$E_3 = 1 - 2\exp(-TI_2/T_{1b})[1 - \exp(-TI_1/T_{1b})]. \quad [15]$$

For the fifth mode, a train of off-resonance saturation pulses causes magnetization exchange between water and macromolecules in a brain tissue but does not affect magnetizations of fat and cerebrospinal fluid. It is a common knowledge in the art of magnetic resonance physics that fat and fluids do not exhibit a magnetization transfer effect. Accordingly, a signal equation for the fifth radiofrequency can be written as:

$$S_5 = PD_b M_{zb}^F + PD_{fat} + PD_{csf} \quad [16]$$

where $M_{zb}^F$ is the normalized steady-state longitudinal magnetization of a brain tissue that is described by the model given by equations [3]-[6] with parameters $t_s$ and $\alpha_3$ equal to zero and that is a function of MPF. To compute MPF from equations [7]-[16], one should take into account the fact that longitudinal relaxation times of fat and cerebrospinal fluid are substantially constant across humans. Accordingly, attenuation factors $E_{fat}$ and $E_{csf}$ can be predetermined for a particular measurement apparatus operating at a particular magnetic field strength and uniformly applied in subsequent signal processing. Based on this fact, in the described exemplary embodiment, three algebraic combinations of signals $S_1$, $S_2$, $S_3$, $S_4$, and $S_5$ are further defined:

$$Q_1 = S_1 - S_2/E_{fat} - S_3/E_{csf}(1 - E_1/E_{fat} - E_2/E_{csf}), \quad [17]$$

$$Q_2 = S_4 = PD_b E_3, \text{ and} \quad [18]$$

$$Q_3 = S_1 - S_2 = PD_b(1 - M_{zb}^F) \quad [19]$$

Quantities $Q_1$, $Q_2$, and $Q_3$ are independent of signal contributions from fat and cerebrospinal fluid and represent only signal parameters associated with a brain tissue. Equations [17] and [18] can be iteratively solved by any non-linear fitting algorithm relative to parameters $PD_b$ and $T_{1b}$. Subsequently, $PD_b$ and $T_{1b}$ values are supplied into equation [19], which is iteratively solved relative to MPF similar to equation [2]. In summary, this exemplary embodiment demonstrates that MPF in a brain tissue of an object can be determined from a non-localized magnetic resonance signal and contributions to MPF from non-brain tissue can be effectively eliminated.

Thus, image-based MPF mapping is converted into a non-imaging method, where the measured signals are collected from the entire brain parenchyma, while unwanted signal components from non-brain tissues are suppressed by the appropriate RF pulse sequence.

The systems and methods described above may be used to study myelination in a body region of a subject, and may be used to study a subject at risk of any brain tissue pathology, including but not limited to multiple sclerosis, brain trauma, stroke, brain degeneration, as well as neurological disorders such as Alzheimer disease and Huntington disease. Additionally, the systems and methods described above may be used to monitor myelination in infants and predict capacities thought to contribute to adult productivity and intelligence.

II. Examples

In a recent study, a high-resolution whole-brain MPF mapping method that utilizes a minimal number of source images to reduce scan time was conducted. The study is discussed in the conference proceedings, Yarnykh V. L., *Fast High-Resolution Whole-Brain Macromolecular Proton Fraction Mapping Using a Minimal Number of Source Images, Proceedings of the 22th Annual Meeting of ISMRM-ESMRMB*, Milan, Italy, 2014; p. 3335, which is incorporated herein by reference in its entirety.

The method applied in the study was a single-point method, wherein an MPF map was obtained by iteratively solving the pulsed magnetization transfer matrix equation using the Gauss-Newton method, with standardized constraints for non-adjustable two-pool model parameters and corrections for $B_0$ and $B_1$ inhomogeneities. A single-point MPF measurement was obtained from a spoiled gradient echo (GRE) MT-weighted image, a reference GRE image for data normalization, and an independently acquired $T_1$ or $R_1$ (wherein $R_1 = 1/T_1$) map.

A time efficient approach to measure $T_1$ or $R_1$ is the two-point variable flip-angle (VFA) method, employing a $T_1$-weighted and a proton density (PD)-weighted GRE image.

The proposed algorithm synthesizes a reference GRE image from $T_1$ or $R_1$ and PD maps with the repetition time and VFA corresponding to those for the MT-weighted image according to the Ernst equation. If VFA data are processed with $B_1$ correction, a $B_1$ map can also be used to calculate a synthetic reference GRE image with actual flip angles in each voxel. Thus, if a synthetic reference GRE image is used, only three source images (MT, $T_1$, and PD-weighted) are needed for MPF mapping.

In the study, MPF maps were obtained based on data from 6 healthy subjects (1 female, 5 males, age range 32-63 years). Images were acquired on a 3T (Philips® Achieva) scanner with an 8-channel head coil. PD and $T_1$-weighted GRE images were acquired with repetition time (TR)=21 ms and FA=4° and 25°, respectively. MT-weighted GRE images were acquired with TR=28 ms, FA=10°, and an off-resonance saturation pulse with single-lobe sinc-gauss shape, an offset frequency of 4 kHz, an effective saturation FA 560°, and a duration of 12 ms. Reference GRE images (TR=28 ms, FA=10°) without saturation were also obtained for comparison purposes. All images were acquired in the 3D mode with non-selective excitation, FOV=240×240×180 mm³, and an isotropic voxel size of 1.25×1.25×1.25 mm³. To gain signal-to-noise ratio (SNR), a dual-echo acquisition (first/second echo time $TE_1/TE_2$=2.3 ms/6.9 ms) was used with summation of individual echo images during reconstruction. Dual-echo $B_0$ maps and actual flip-angle imaging (AFI) $B_1$ maps were acquired with voxel sizes of 2.5×2.5×2.5 mm³ and 2.5×2.75×5.0 mm³, respectively. Parallel imaging was used in both phase encoding directions with acceleration factors of 1.5 (anterior-posterior) and 1.2 (left-right). Scan times were 4 min 21 s for the $T_1$ and PD-weighted images, 5 min 48 s for the MT-weighted image and the reference image, 2 min 8 s for the $B_0$ map, and 3 min 26 s for the $B_1$ map, thus resulting in an about 20 min acquisition time for the entire protocol without the reference image.

Figure 5:
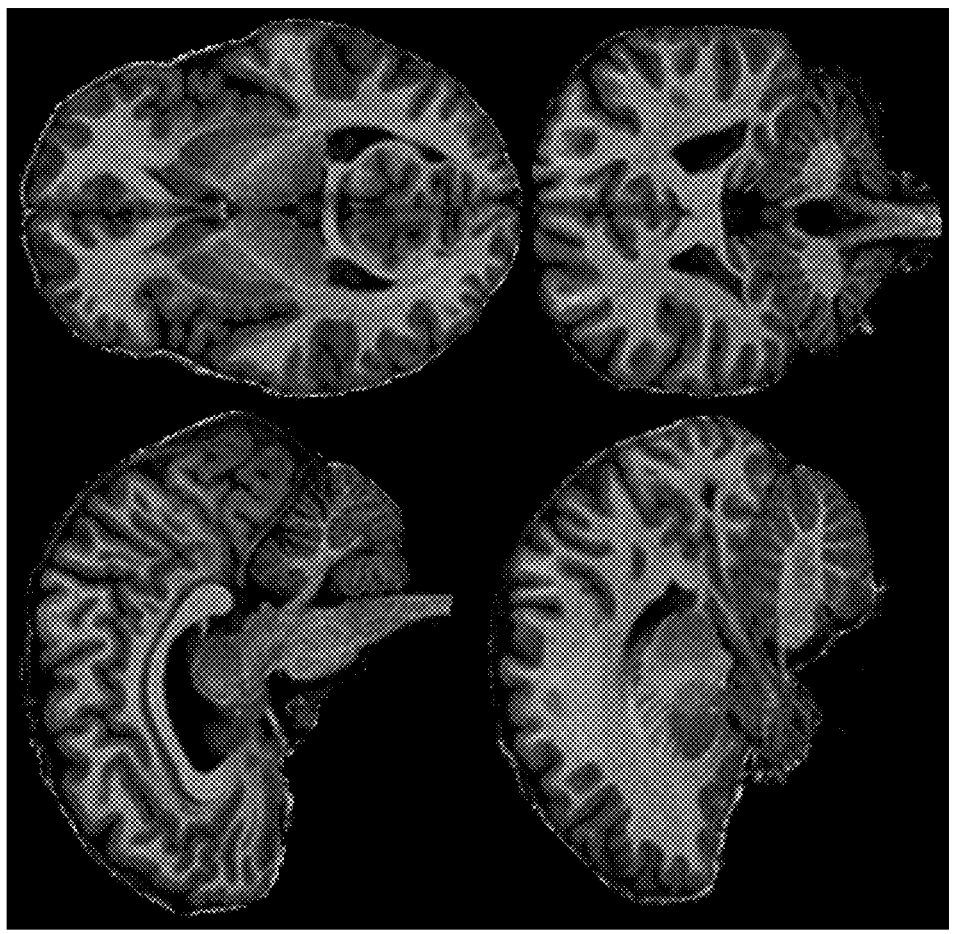
FIG. 5 depicts an image comprising reformatted views of a high-resolution 3D MPF map in accordance with an example embodiment.

FIG. 5 depicts an image 500 comprising reformatted views of a high-resolution 3D MPF map, in accordance with an example embodiment. The image 500 was obtained with the synthetic reference image method described above. The image 500 demonstrates sharp white matter to gray matter (WM/GM) contrast and clear visualization of anatomical details of the brain.

Figure 6:
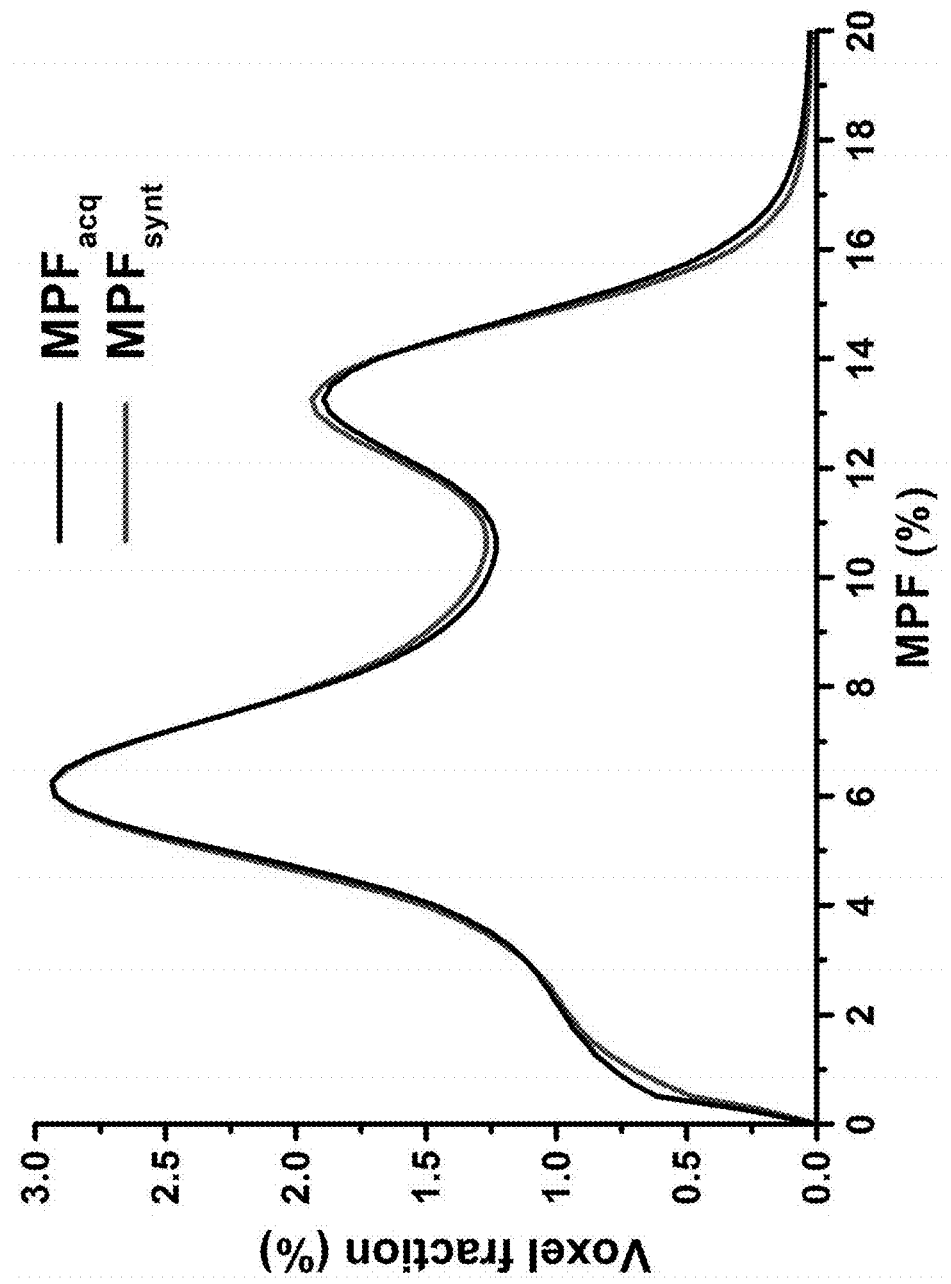
FIG. 6 depicts a graph illustrating voxel fraction percent plotted over percent MPF in accordance with at least one embodiment.

FIG. 6 depicts a graph 600 illustrating voxel fraction percentage plotted over MPF percentage, in accordance with at least one embodiment. In the graph 600, group whole-brain MPF histograms were computed from MPF maps reconstructed using acquired ($MPF_{acq}$) and synthetic ($MPF_{synt}$) reference images and were averaged across the 6 healthy subjects. This group whole-brain MPF histogram demonstrates a very close agreement between the acquired and the synthetic reference images.

Another study, Yarnykh, Vasily L., *Time-Efficient, High-Resolution, Whole Brain Three-Dimensional Macromolecular Proton Fraction Mapping*, Magnetic Resonance in Medicine (2015), which is which is incorporated herein by reference in its entirety, discusses results obtained using systems and methods such as those described with reference to FIGS. 1-6. MPF maps were obtained based on data from 8 healthy subjects (4 females, 4 males, age range 29-66 years). Additionally, standard anatomical high-resolution 3D magnetization prepared rapid acquisition gradient echo (MPRAGE) $T_1$ weighted images (TR/TE=5.9 ms/2.8 ms, FA=8°, inversion time (TI)=900 ms, shot interval=2500 ms, voxel size=1×1×1 mm³, scan time=4 min 44 s) were acquired with the same field of view for comparison purposes.

MPF maps were reconstructed with the standard method based on the acquired reference image and the synthetic reference method described above. Previously determined constraints for non-adjustable two-pool model parameters and their combinations were used in both algorithms as follows: cross-relaxation rate constant R=19.0 s⁻¹, product of $R_1$ and $T_2$ of free water protons $R_1 T_2^F$=0.022, and $T_2$ of bound macromolecular protons $T_2^B$=10 μs.

Before reconstruction, non-brain tissues were removed from source images by applying a brain mask created from the PD-weighted image. Additionally, CSF was segmented out from $R_1$ maps based on a threshold value of $R_1$=0.33 s⁻¹ (equivalent to $T_1$=3000 ms). MPF maps reconstructed with both methods were segmented into WM and GM. Segmentation was performed by an automated segmentation tool using software in the native image space with a Markov random field weighting parameter 0.25. To account for potentially incomplete CSF segmentation by $R_1$ threshold and exclude voxels containing partial volume of CSF (PVCSF), a third mixed tissue class was also prescribed. Tissue classes were defined by specifying initial tissue-type priors with the following MPF values: 12% for WM, 6% for GM, and 1% for PVCSF. Resulting binary segmentation masks were used to calculate mean MPF in WM and GM.

A statistical analysis was carried out in SPSS software. Normality of data distribution was checked using the Shapiro-Wilk test to justify parametric analyses. An agreement between MPF map reconstruction techniques with acquired and synthetic reference images was assessed using Bland-Altman plots. The bias between MPF values in segmented WM and GM measured from MPF maps reconstructed by the two methods was examined using the one sample t-test for the mean difference between paired measurements. The limits of agreement were calculated as the mean difference ±1.96 standard deviation of the mean difference. To estimate variability between measurements from the two reconstruction options, the within-subject coefficients of variation (CV) was calculated as the percentage ratio of standard deviation to the mean of paired measurements. The Levene's test was used to assess equality of variances. P values less than 0.05 were considered statistically significant.

Figure 7:
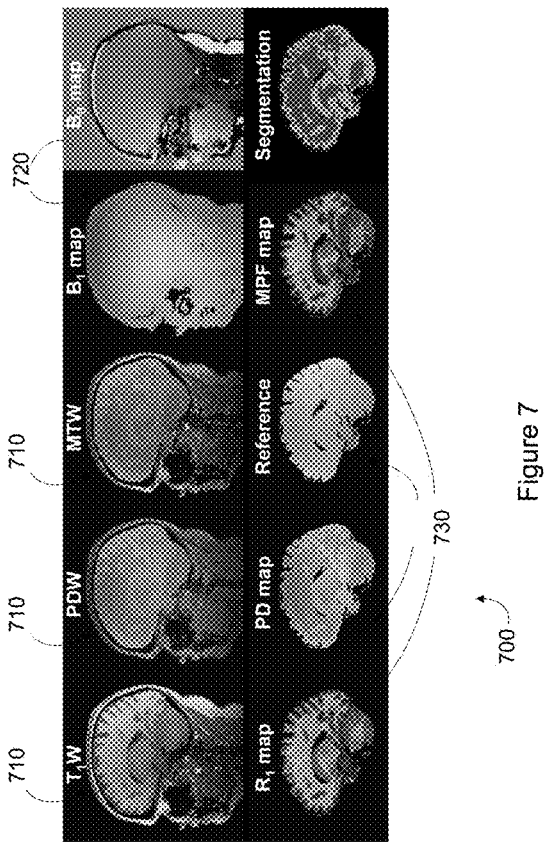
FIG. 7 depicts a series of images obtained from a system such as the system of FIG. 1 in accordance with at least one embodiment.

FIG. 7 depicts a series of images 700 obtained from a system such as the system 100 of FIG. 1, in accordance with at least one embodiment. The images were obtained from the study discussed above and depict the minimal set of three source images 710 (representing $T_1$-weighted ($T_1$W), PD-weighted (PDW), and MT-weighted (MTW) GRE images), $B_0$ and $B_1$ field maps 720, and corresponding parametric maps 730 that were generated by the algorithm based on the source images and field maps. The parametric maps 730 include $R_1$ and PD maps reconstructed from $T_1$W and PDW images, a synthetic reference image, a resulting MPF map, and a binary segmentation mask corresponding to WM, GM, and PVCSF tissue classes. The images 700 are presented with removed extra-cranial tissues and CSF.

Figure 8:
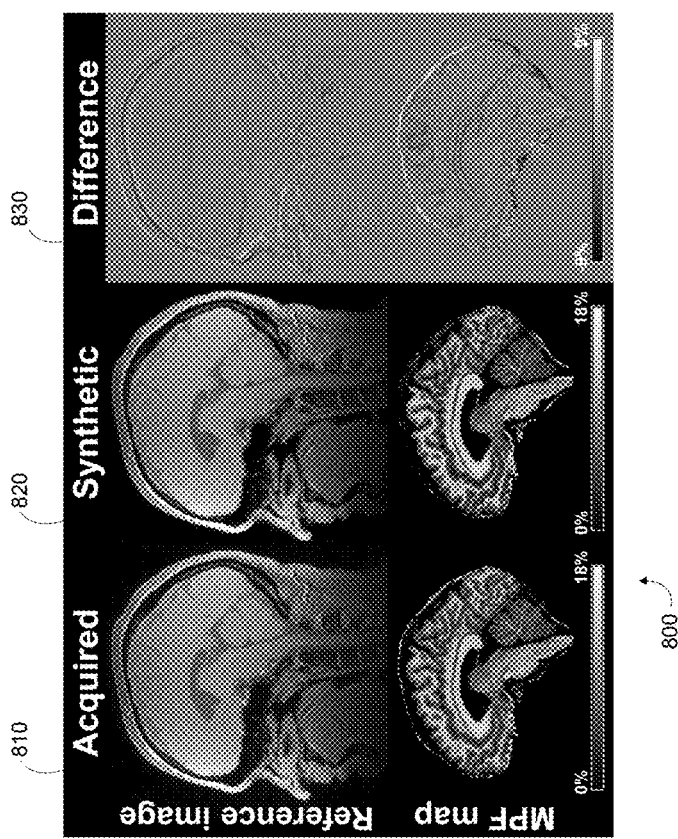
FIG. 8 depicts a comparison table comparing acquired and synthetic images and MPF maps reconstructed with the acquired and synthetic images in accordance with at least one embodiment.

FIG. 8 depicts a comparison table 800 comparing acquired and synthetic images and MPF maps reconstructed with the acquired and synthetic images, in accordance with at least one embodiment. In the comparison table 800, acquired images, in column 810, and synthetic reference images, in column 820, are present in the top row of the table, and MPF maps reconstructed with the associated images are depicted below for each respective column.

Column 830 of the comparison table 800 shows subtraction images to demonstrate the difference between the acquired and synthetic images and maps reconstructed from each. Only minor discrepancies associated with sub-voxel misregistration are seen on the tissue borders in column 830. Grayscale ranges correspond to MPF of 0-18% for the maps and −9-9% for their difference.

Figure 9:
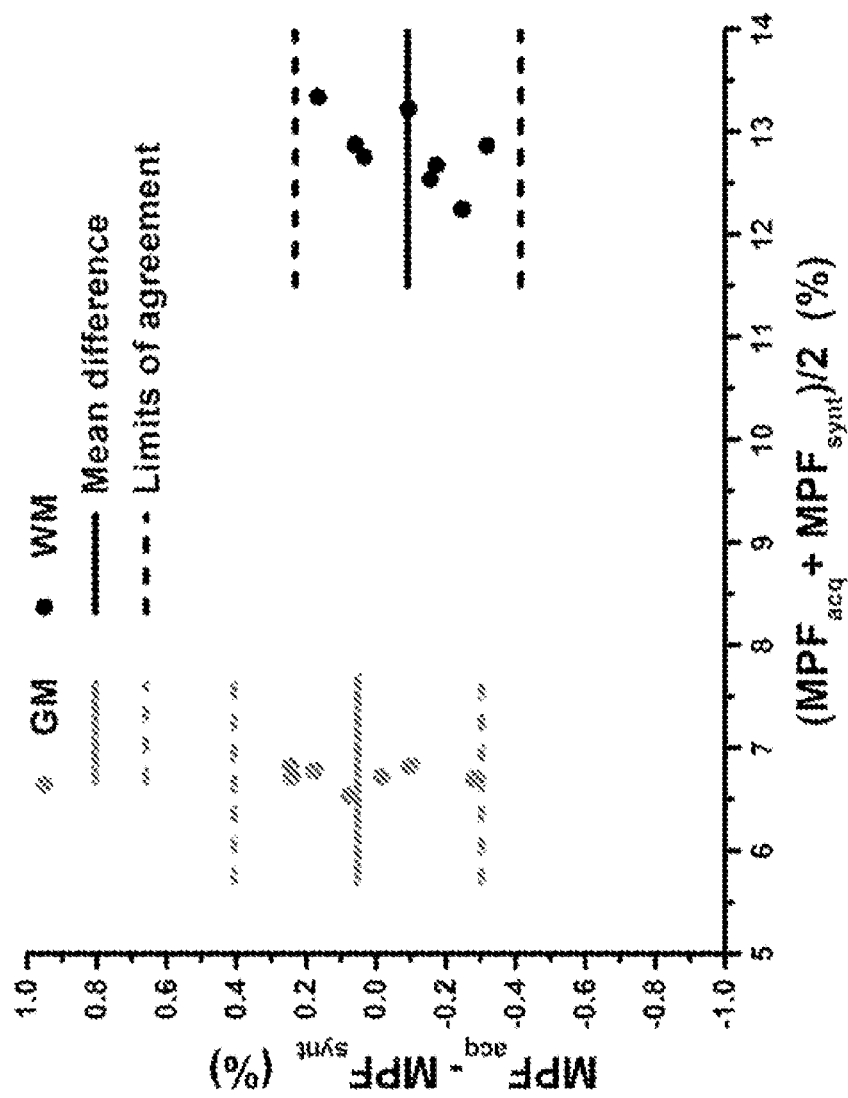
FIG. 9 depicts a graph illustrating percent ($MPF_{acq}-MPF_{synt}$) plotted over percent ($MPF_{acq}+MPF_{synt}$)/2 in accordance with at least one embodiment.

FIG. 9 depicts a graph 900 illustrating percent ($MPF_{acq}-MPF_{synt}$) plotted over percent ($MPF_{acq}+MPF_{synt}$)/2, in accordance with at least one embodiment. MPF in WM (black symbols) and GM (gray symbols) demonstrated close agreement with no significant bias between reconstruction methods, equal variances, and small within-subject coefficients of variation. Solid and dashed lines correspond to the mean difference and limits of agreement, respectively.

FIG. 10 depicts a table 1000 illustrating a comparison between MPF measurements with acquired and synthetic reference images in segmented brain tissues in accordance with at least one exemplary embodiment. Results of quantitative MPF measurements in segmented WM and GM based on the maps reconstructed with acquired and synthetic reference images are provided in the table 1000.

Figure 11:
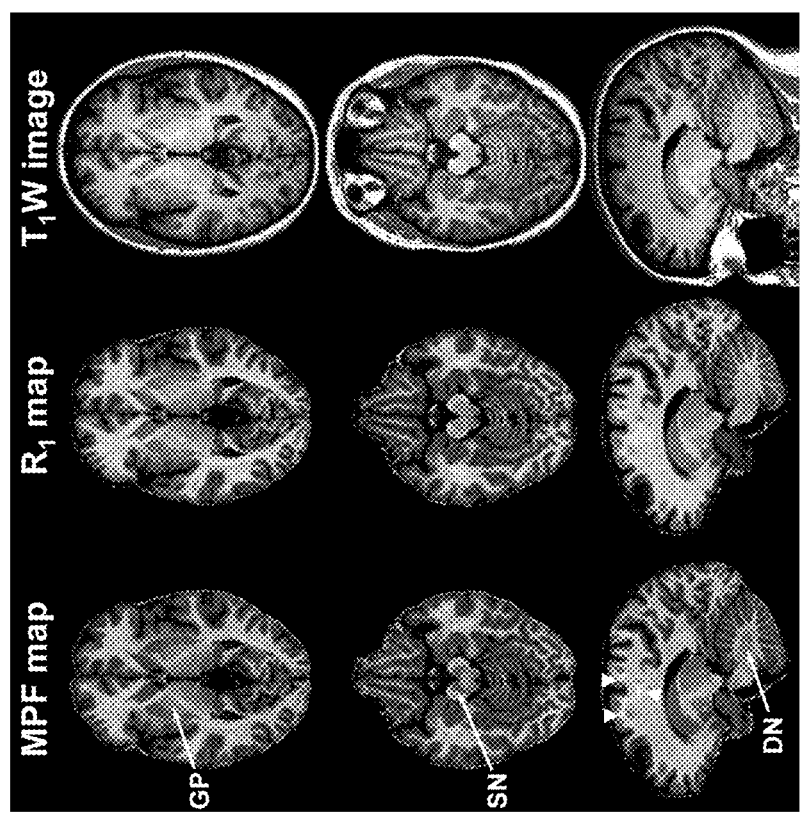
FIG. 11 depicts reformatted sections of a 3D MPF map, an $R_1$ map, and a $T_1$-weighted image comparing tissue contrast for iron-rich GM anatomical structures, in accordance with at least one embodiment.

FIG. 11 depicts reformatted sections 1100 of a 3D MPF map, $R_1$ map, and $T_1$-weighted image comparing tissue contrast for iron-rich GM anatomical structures. Arrows indicate the globus pallidus (GP), substantia nigra (SN), and dentate nucleus (DN). Arrowheads indicate intrinsic variations of MPF within WM. As shown in FIG. 11, the MPF maps can produce pure GM contrast for subcortical structures with high iron content, such as GP, SN, and DN. These structures appear clearly hypointense on MPF maps compared to WM, similar to the rest of GM. In contrast, iron-rich GM structures are undistinguishable or poorly distinguishable from surrounding WM on both $T_1$-weighted anatomical images and $R_1$ maps. FIG. 11 also shows the contrast variations within WM due to a variable degree of myelination. Such an inherent WM signal variability is much less clear or invisible on $T_1$-weighted anatomical images and $R_1$ maps.

In yet another study, Yarnykh V. L., *Three-Dimensional Macromolecular Proton Fraction Mapping of the Human Cervical Spinal Cord, Proceedings of the 22th Annual Meeting of ISMRM-ESMRMB*, Milan, Italy, 2014; p. 3449, hereby incorporated by reference in its entirety, systems and methods such as those discussed above with reference to FIGS. 1-2 are evaluated. In this study, single-point MPF mapping was combined with two-point variable flip-angle (VFA) $T_1$ mapping. High signal-to-noise ratio (SNR) is important for the accuracy of single-point MPF mapping and the use of source images with SNR>100 has been recommended. To gain SNR, the multiple gradient echo summation technique was applied. To reduce scan time, single-point MPF mapping was modified to avoid acquisition of a reference image by using a synthetic reference image.

The pulsed magnetization transfer matrix equation was iteratively solved by the Gauss-Newton method and standardized constraints for non-adjustable two-pool model parameters, as well as corrections for $B_0$ and $B_1$ inhomogeneities, to yield an MPF map. As input data, a single-point MPF measurement requires a GRE MT-weighted image, a reference GRE image for data normalization, and an independently acquired $T_1$ map. The two-point VFA $T_1$ mapping method utilizes a $T_1$-weighted image due to the absence of a long off-resonance saturation pulse. Instead of acquiring a reference image with TR and flip angle (FA) corresponding to those for the MT-weighted image, it can be synthesized from $T_1$ and PD maps reconstructed from VFA data according to the Ernst equation.

Data was obtained from 4 healthy subjects (2 females, 2 males, age 39-52 years). Images of the cervical spinal cord were acquired on a 3T scanner with a manufacturer's phased array spine coil. PD and $T_1$-weighted GRE images were acquired with TR=20 ms and FA=3° and 20°, respectively. MT-weighted GRE images were acquired with TR=40 ms, FA=10°, and off-resonance saturation pulse with single-lobe sinc-gauss shape, offset frequency 4 kHz, effective saturation FA 560°, and a duration of 18 ms. All images were acquired in the 3D mode with FOV=140×140×160 mm$^3$, and voxel size of 1×1×2 mm$^3$. Four-echo acquisition acquisition was used in the sequences. Dual-echo $B_0$ maps and actual flip-angle imaging (AFI) $B_1$ maps were acquired with voxel size of 1.5×1.5×4 mm$^3$. Scan times were 3 min 45 s for the $T_1$ and PD-weighted images, 7 min 30 s for the MT-weighted image, 2 min 25 s for the $B_0$ map, and 4 min 45 s for the $B_1$ map, thus resulting in about a 22 min acquisition time for the entire protocol.

To evaluate performance of multiple echo summation, MPF map reconstructions were carried out with the first echo image only and sums of 2, 3, and 4 echoes. SNRs in the spinal cord relative to the background noise were estimated on MT-weighted images at the central location of the slab. MPF values in anatomical structures of the spinal cord were measured on the MPF maps. Measurements were performed in WM regions of interest corresponding to ventral, lateral, and dorsal columns and GM regions of interest corresponding to ventral and dorsal horns. A series of paired t-tests on bilaterally averaged data pooled across subjects and levels was used to assess regional differences between anatomical structures.

Figure 12:
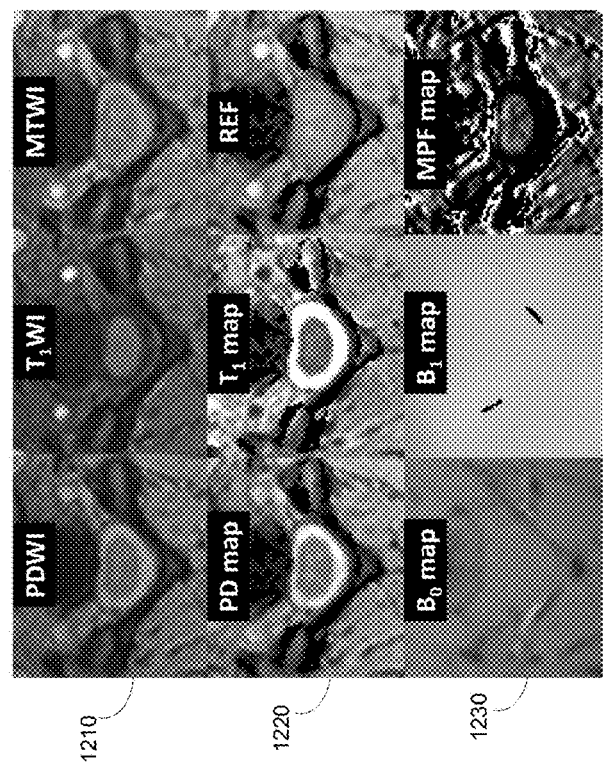
FIG. 12 depicts an overview of the spinal cord MPF mapping in accordance with at least one exemplary embodiment.

FIG. 12 depicts an overview of the spinal cord MPF mapping 1200, in accordance with at least one exemplary embodiment. FIG. 12 shows component images involved in data acquisition and MPF map reconstruction. The top row 1210 shows acquired source GRE images: PD-weighted (PDWI), $T_1$-weighted ($T_1$WI), and MT-weighted (MTWI). The middle row 1220 shows intermediate parametric images reconstructed from VFA data (PD map, $T_1$ map, and a synthetic reference image). The bottom row 1230 shows $B_0$ and $B_1$ field maps and a resulting MPF map. A dramatic increase of the contrast between WM and GM in the spinal cord compared to source images or other parametric maps ($T_1$ and PD). Multiple echo summation allowed about 1.4, 1.6, and 1.8-fold SNR gain in source images for 2, 3, and 4 echoes, respectively.

Figure 13:
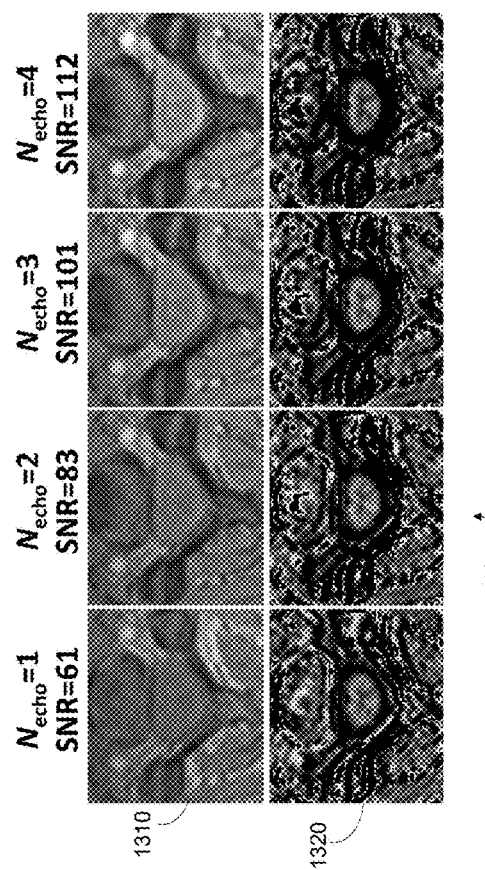
FIG. 13 depicts images of the effect of multiple echo summation on the SNR, MT-weighted contrast, and quality of MPF maps in accordance with at least one exemplary embodiment.

FIG. 13 depicts images 1300 of the effect of multiple echo summation on the SNR, MT-weighted contrast, and quality of MPF maps, in accordance with at least one exemplary embodiment. In FIG. 13, the use of multiple echo summation visibly improves MT-weighted contrast on source images and anatomical consistency of spinal cord structures on reconstructed MPF maps. A top row 1310 shows MT-weighted images corresponding to the first-echo ($N_{echo}$=1) and summation of 2, 3, and 4 echoes ($N_{echo}$=2, 3, and 4) with SNR values in the spinal cord. A bottom row 1320 shows MPF maps reconstructed from the images in the top row 1310.

FIG. 14 depicts images 1400 of anatomic appearance of WM and GM on MPF maps of the cervical spinal cord at different levels, in accordance with at least one exemplary embodiment. In FIG. 14, representative axial sections of the 3D MPF map of the cervical spinal cord at the levels of C2, C3, C4, and C5 vertebra were obtained from a healthy subject. The image 1410 depicts a reformatted middle sagittal section of the same 3D MPF map.

This study demonstrates feasibility of 3D MPF mapping of the human spinal cord in vivo. By using the minimal possible dataset comprising only three source images and multiple echo summation, the described approach enables sufficient resolution and SNR with a reasonable scan time. Quantitative myelin assessment and high-contrast neuroanatomical imaging are combined for a variety of spinal cord applications.

Besides quantitative tissue characterization, high-resolution MPF mapping has a potential to become a useful technique for various neuroscience applications including segmentation of cortical, subcortical, cerebellar, and brain stem structures. The use of MPF maps as source images in such applications may be advantageous due to a very high tissue contrast and insensitivity to iron. Another important advantage of MPF maps as source images is the inherent correction of field and coil reception non-uniformities. Specifically, spatial variations of $B_0$ and $B_1$ fields are corrected based on the rigorous physical model by directly accommodating corresponding field maps into the image reconstruction workflow. The effect of the coil reception profile is eliminated by normalization to the synthetic reference image and does not propagate into resulting MPF maps. As such, the use of MPF maps eliminates the need in computationally-intense bias field correction algorithms and allows utilization of native quantitative voxel values in various post-processing tasks.

In yet another study, first reported herein, systems and methods such as those discussed above with reference to FIGS. 1-3 are evaluated. In this study, a feasibility of measuring age-related changes in brain myelination in children using non-localized whole-head MPF measurements was assessed. As a model of a non-localized magnetic resonance signal measurement, a whole-head three dimensional image was used, and intensities of all voxels in such an image were averaged to yield a single value proportional to a magnitude signal that could be obtained from an entire head without applying magnetic field gradients. Data were acquired using three radiofrequency modes as depicted in FIG. 3 and processed using equations [1]-[6], as specified above. A clinical MRI scanner (Toshiba® Vantage Titan) with 1.5T magnetic field strength was used for data acquisition. The three radiofrequency modes depicted in FIG. 2 were executed with following parameters: $\alpha_1=3°$ and TR=16 ms for the first mode; $\alpha_2=18°$ and TR=16 ms for the second mode; and $\alpha_3=8°$, TR=20.5 ms, $\Delta_{mt}=2$ kHz, $\alpha_{mt}=200°$, and $t_{mt}=1.5$ ms for the third mode. 3D images corresponding to each mode were obtained with a large field-of-view covering the whole head and isotropic spatial resolution of 1.4 mm$^3$. Data were obtained from 23 children aged from one week to 14 years. All participants underwent MRI for various clinical indications but were free from radiological abnormalities of the brain according to evaluation by certified neuroradiologists.

Figure 15:
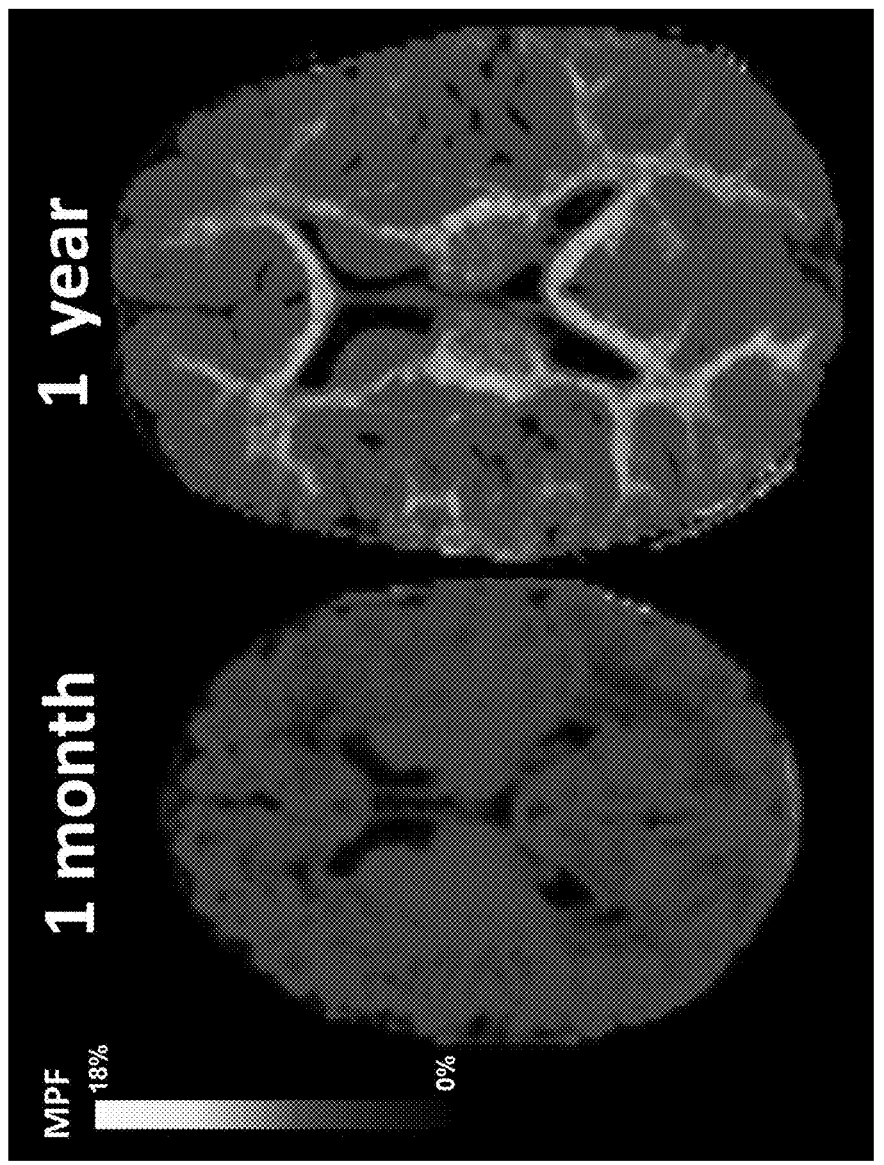
FIG. 15 depicts example cross-sections of 3D MPF maps obtained from a subject of one month and a subject of one year of age.

FIG. 15 depicts example cross-sections 1500 of color-coded 3D MPF maps obtained from subjects of one month and of one year of age. A dramatic increase of MPF caused by the development of myelin in white matter is easily visible in FIG. 15 by comparing MPF maps from the subjects of different age.

Figure 16:
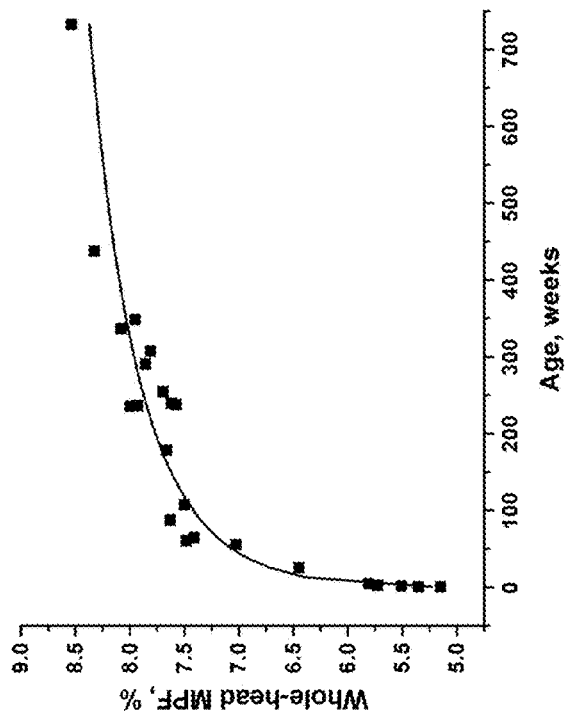
FIG. 16 depicts a graph illustrating a dependence of whole-head MPF values obtained from average intensities of all voxels in 3D images in accordance with at least one exemplary embodiments.

FIG. 16 depicts a graph 1600 illustrating a dependence of the whole-head MPF values obtained from average intensities of all voxels in 3D images on the age for 23 children, wherein each point represents a whole-head MPF measurement for a single study participant. A solid line in FIG. 16 depicts a plot of a generalized logistic model fitted to experimental data. FIG. 16 illustrates that dramatic changes in brain myelination over the first year of life can be reliably captured by non-localized whole-head MPF measurements.

Figure 17:
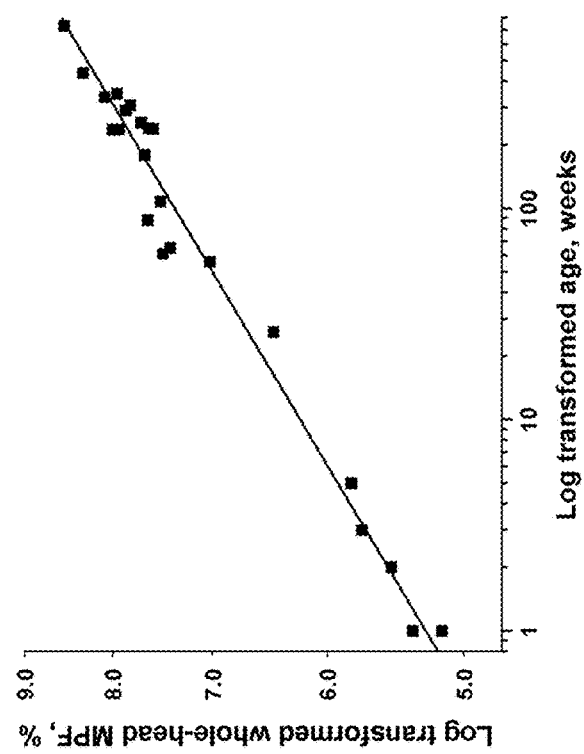
FIG. 17 depicts a graph of Pearson's correlation between whole-head MPF measurements and a subject's age after logarithmic transformation of data in accordance with at least one exemplary embodiment.

FIG. 17 depicts a graph 1700 of Pearson's correlation between whole-head MPF measurements and age after a logarithmic transformation of the data presented FIG. 16. The correlation coefficient is high (r=0.987), thus indicating that whole-head MPF values describe the process of brain myelination with high quantitative accuracy.

This study demonstrates that the MPF measured from the whole-head magnetic resonance signal is representative of the whole-brain MPF and provides a realistic non-invasive measure of the brain myelination process during the childhood. Even without suppression of unwanted signals from tissues not belonging to the brain, a prototype non-localized method for MPF measurements, such as that depicted in FIG. 3, accurately characterizes quantitative age-related changes in the brain myelin content. Further implementation of an advanced method with suppression of unwanted tissue signals, as depicted in FIG. 4, is expected to improve sensitivity of non-localized MPF measurements to more subtle changes in myelination, particularly to those associated with a delayed development in children and neurological disease in adults.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A method for measuring macromolecular proton fraction (MPF) in a subject, the method comprising:
applying, via a nuclear magnetic resonance apparatus, a magnetic field to a body region of the subject, the body region including a first tissue and a second tissue;
applying a first radiofrequency (RF) mode and a second RF mode to the body region such that (i) the first RF mode causes suppression of signal components returned from the first tissue, and (ii) the second RF mode causes magnetization exchange between water and macromolecules in the second tissue;
detecting a plurality of magnetic signals emitted from the body region in response to applying the first RF mode and the second RF mode to the body region; and
calculating an MPF in the body region based on the plurality of magnetic signals.

2. The method of claim 1, wherein the body region encompasses one or both of a brain or a spinal cord of the subject.

3. The method of claim 2, wherein the first tissue does not belong to the brain of the subject.

4. The method of claim 3, wherein the first tissue comprises one or more of: (i) a fat tissue; (ii) a muscle tissue; and (iii) cerebrospinal fluid.

5. The method of claim 2, wherein applying the first RF mode and the second RF mode causes one or more of the following: (i) a saturation of a nuclear magnetization of fat protons outside the brain; (ii) a saturation of a nuclear magnetization of muscle protons outside the brain; (iii) a saturation of a nuclear magnetization of cerebrospinal fluid protons inside the brain; (iv) a variable excitation of a nuclear magnetization of protons of the brain; or (v) a variable saturation of a nuclear magnetization of macromolecular protons in the brain parenchyma.

6. The method of claim 2, wherein detecting the plurality of magnetic signals is performed after varying one or more of the following: (i) excitation of nuclear magnetization of protons of the brain; (ii) saturation of nuclear magnetization of macromolecular protons in brain parenchyma; or (iii) a duration of a time delay separating pulses of the first RF mode or the second RF mode.

7. The method of claim 1, wherein the subject is a human subject.

8. The method of claim 1, further comprising:
comparing the MPF with a control.

9. The method of claim 1, further comprising:
determining a myelin content in the body region based on the MPF.

10. The method of claim 1, further comprising:
using the plurality of magnetic signals to calculate a proton density of the body region and a longitudinal relaxation time of the body region, and
wherein calculating the MPF comprises using the proton density and the longitudinal relaxation time to calculate the MPF.

11. A magnetic resonance apparatus comprising:
a magnet;
a radiofrequency pulse generator; and
a processor and a non-transitory computer-readable medium storing program instructions thereon executable by the processor to cause the apparatus to perform functions comprising:
applying, via the magnet, a magnetic field to a body region of a subject, the body region including a first tissue and a second tissue;
applying a first radiofrequency (RF) mode and a second RF mode to the body region such that (i) the first RF mode causes suppression of signal components returned from the first tissue and (ii) the second RF mode causes magnetization exchange between water and macromolecules in the second tissue;
detecting a plurality of magnetic signals emitted from the body region in response to applying the first RF mode and the second RF mode to the body region; and
calculating an MPF in the body region based on the plurality of magnetic signals.

12. The magnetic resonance apparatus of claim 11, wherein the first tissue comprises one or more of: (i) a fat tissue; (ii) a muscle tissue; or (iii) cerebrospinal fluid.

13. The magnetic resonance apparatus of claim 11, wherein the body region encompasses one or both of a head or a spinal cord of the subject.

14. The magnetic resonance apparatus of claim 11, the functions further comprising:
using the plurality of magnetic signals to calculate a proton density of the body region and a longitudinal relaxation time of the body region, and
wherein calculating the MPF comprises using the proton density and the longitudinal relaxation time to calculate the MPF.

15. A method for measuring macromolecular proton fraction in a subject, the method comprising:
applying a magnetic field to a body region of a subject, the body region including a first tissue and a second tissue;
applying a first plurality of radiofrequency pulses at a nuclear magnetic resonance frequency so that the first plurality of radiofrequency pulses causes nutation of a nuclear magnetization in the body region by a first flip angle;
detecting a first magnetic resonance signal emitted from the body region in response to applying the first plurality of radiofrequency pulses;
applying a second plurality of radiofrequency pulses at the nuclear magnetic resonance frequency so that the second plurality of radiofrequency pulses causes nutation of a nuclear magnetization in the body region by a second flip angle that is different from the first flip angle;
detecting a second magnetic resonance signal emitted from the body region in response to applying the second plurality of radiofrequency pulses;
applying a plurality of saturation radiofrequency pulses at a frequency that is different from the nuclear magnetic resonance frequency so that the plurality of saturation radiofrequency pulses causes saturation of a nuclear magnetization of macromolecular protons in the body region;
applying a third plurality of radiofrequency pulses at the nuclear magnetic resonance frequency so that the third plurality of radiofrequency pulses causes nutation of a nuclear magnetization in the body region by a third flip angle that is different from the first flip angle and the second flip angle, wherein each pulse of the third plurality of radiofrequency pulses is applied after a first pulse of the plurality of saturation radiofrequency pulses and before a second pulse of the plurality of saturation radiofrequency pulses;
detecting a third magnetic resonance signal emitted from the body region in response to applying the third plurality of radiofrequency pulses and the plurality of saturation radiofrequency pulses; and
calculating the macromolecular proton fraction by using the first magnetic resonance signal, the second magnetic resonance signal, and the third magnetic resonance signal.

16. The method of claim 15, further comprising:
spatially encoding the first magnetic resonance signal, the second magnetic resonance signal, and the third magnetic resonance signal; and
constructing a map comprising a spatial distribution of the macromolecular proton fraction values.

17. The method of claim 16, wherein the body region is a brain of the subject.

18. The method of claim 17, further comprising:
suppressing signal components from tissues not belonging to the brain by magnetization preparation.

19. The method of claim 18, wherein magnetization preparation includes one of the following: (i) inversion-recovery; (ii) partial inversion-recovery; and (iii) spectrally-selective saturation.

20. A method of mapping macromolecular proton fraction using only three source images, comprising:
reconstructing longitudinal relaxation time and proton density maps from two variable flip angle source images;
synthesizing a synthetic reference image from the longitudinal relaxation time and proton density maps; and
reconstructing a macromolecular proton fraction map from a magnetization transfer (MT) weighted image normalized to the synthetic reference image and the longitudinal relaxation time map,
wherein reconstructing the longitudinal relaxation time and proton density maps from the two variable flip angle source images further comprises processing the two variable flip angle source images with corrections for magnetic and radiofrequency field inhomogeneities, and wherein synthesizing the synthetic reference image further comprises synthesizing the synthetic reference image from the longitudinal relaxation time map, the proton density map, and a radiofrequency field inhomogeneity map.

21. The method of claim 20, wherein the method is used to determine the myelin content in a tissue of a human subject.

* * * * *